United States Patent [19]

Hülsmann et al.

[11] Patent Number: 4,643,850

[45] Date of Patent: Feb. 17, 1987

[54] SILANE MODIFIED ESTER MIXTURES, A METHOD FOR THEIR PREPARATION, AND THEIR USE IN PHARMACEUTICAL AND COSMETIC PREPARATIONS

[75] Inventors: Hans L. Hülsmann, Wetter; Reinhard Pass, Witten; Horst Hermsdorf, Bochum-Querenburg, all of Fed. Rep. of Germany

[73] Assignee: Dynamit Nobel AG, Troisdorf Bez Koeln, Fed. Rep. of Germany

[21] Appl. No.: 682,777

[22] Filed: Dec. 18, 1984

[30] Foreign Application Priority Data

Dec. 23, 1983 [DE] Fed. Rep. of Germany ....... 3346641
Dec. 23, 1983 [DE] Fed. Rep. of Germany ....... 3346642

[51] Int. Cl.$^4$ .......................... A61K 9/06; A61K 7/00; A61K 7/40; A61K 7/42
[52] U.S. Cl. .............................. 260/410.7; 260/410.8; 560/199; 424/59; 424/78; 514/63
[58] Field of Search .................. 260/410, 410.6, 410.7, 260/410.8, 410.9 R; 560/199; 424/32, 59, 78; 514/63

[56] References Cited

U.S. PATENT DOCUMENTS 3,258,477  6/1966  Plueddemann et al. ............ 556/440
4,336,309  6/1982  Jäckel et al. ....................... 427/387
4,366,100  12/1982  Naskar et al. ..................... 560/199

FOREIGN PATENT DOCUMENTS 1014712  9/1952  Fed. Rep. of Germany .
1046259  4/1956  Fed. Rep. of Germany .

*Primary Examiner*—John Kight
*Assistant Examiner*—Nathan M. Nutter
*Attorney, Agent, or Firm*—Felfe & Lynch

[57] ABSTRACT

Viscous, gel-like ester mixtures of reaction products of fatty acid polyol partial esters and gamma-glycidoxypropyltrialkoxysilanes, which can contain, if desired, dicarboxylic acids as additional reaction components, and methods for their preparation are disclosed. The ester mixtures are especially provided as additives for oily liquids for the preparation of gels or for increasing viscosity. Also, spreadable preparations are disclosed, which are produced from a component of oily consistency and, preferably, an active agent contained therein, which, because they contain the new ester mixtures, consisting of products of the reaction of partial esters of polyols of the aliphatic monocarboxylic acids and, in some cases, the aliphatic dicarboxylic acids, with gamma-glycidoxypropyltrialkoxysilanes of high ability to adhere to the skin, are difficult to wash from the skin and make the skin difficult to wet.

16 Claims, No Drawings

SILANE MODIFIED ESTER MIXTURES, A METHOD FOR THEIR PREPARATION, AND THEIR USE IN PHARMACEUTICAL AND COSMETIC PREPARATIONS

BACKGROUND OF THE INVENTION

The invention relates to viscous, gel-like ester mixtures and to their preparation.

It is the aim of the invention to produce viscous, gel-like ester mixtures from easily available starting substances by simple methods. The viscous, gel-like substances are used in the technical field, in lubricant formulations among other things, and especially in the cosmetic field, in which its use is contemplated preferentially as a viscous oil component or oleogel. They are also used as pharmaceutical adjuvants.

Known viscous, gel-like ester mixtures on the basis of different fatty acid-polyol partial esters have only limited usefulness. European Pat. No. 0014 308 describes viscous ester mixtures of fatty acid polyol partial esters condensed with dicarboxylic acids, but the control of their viscosity is limited due to such substances becoming thermoplastic polyesters as the incorporation of dicarboxylic acid increases. Furthermore, viscous, gel-like compounds can be prepared from unsaturated oils having dry properties by thermal or oxidative polymerization. It is known to form oleogels from oils and fats and partial esters based thereon, in two-component or multiple component systems, by means of thickening agents such as those, for example, on the basis of soaps, natural lay minerals such as bentonites, silicon oxide or hydroxide, cellulose ether esters, polyurea compounds or ureido or amido compounds. Frequently occurring deficiencies of these oleogel-forming multiple substance systems are lack of transparency, unpleasant feel on the skin, excessively high gelling temperatures, limited possibility for the creation of gel systems of low viscosity, and especially the bleeding of oil from such gels in preparations of active substances.

The problem therefore was to prepare viscous, gel-like ester mixtures of high transparency and high gel stability, with a viscosity which can be adjusted to predetermined levels.

THE INVENTION

The subject of the invention is viscous, gel-like ester mixtures of reaction products of fatty acid polyol partial esters or their mixtures, having hydroxyl numbers from 5 to 150, preferably 10 to 80, and 2 to 45%, preferably 4 to 30%, of the weight of the ester mixtures, of gamma-glycidoxypropyltrialkoxysilanes having alkyl groups of 1 to 3 carbon atoms, or mixtures thereof, as well as ester mixtures which contain as additional reaction components dicarboxylic acids and/or their anhydrides or halides, in amounts of 0.01 to 50 mole-%, preferably 0.01 to 30 mole-%, per mole of the hydroxyl groups of the polyols.

As the hydroxyl numbers of the reacted partial esters increase from 5 to 150, while the contents of gamma-glycidoxypropyltrialkoxysilanes increase accordingly from 2 to 45 wt.-%, ester mixtures of increasing viscosity are obtained. If dicarboxylic acids are contained as reaction components, their increasing content results in a lesser increase of the viscosity, but particularly in low turbidity points.

The viscosities of the ester mixtures of the invention are accordingly variable and reproducible by the selection of the components and their proportions.

The term, "fatty acid polyol partial ester," refers to the class of the hydroxyl-group-containing fatty acid esters of difunctional to hexafunctional alcohols and their ether polyols. Polyvalent alcohols, i.e., polyols, are, for example, propanediol, glycerol, trimethylolpropane, pentaerythritol or sorbitol. The spectrum of the acids which can be esterified to partial esters includes saturated, unsaturated, straight-chain and branched-chain, aliphatic and cycloaliphatic monocarboxylic acids of 2 to 22 carbon atoms, or their mixtures, as well as, in some cases, additionally esterifiable saturated, unsaturated, aliphatic and/or aromatic dicarboxylic acids, preferably aliphatic dicarboxylic acids having 2 to 20, and especially 3 to 8, carbon atoms. The viscous, gel-like ester mixtures of interest in the cosmetic field contain especially polyols such as 1,2-propanediol, mono-, di- and triethyleneglycols or glycerol, and especially fatty acids of an aliphatic, straight-chain or branched-chain, especially saturated kind, having 6 to 18 carbon atoms. In addition, dicarboxylic acids can be included in the partial esterification, such as succinic acid, adipic acid or sebacic acid.

Viscous, gel-like ester mixtures which find application in the technical sectors can contain polyols, such as for example trimethylolpropane, pentaerythritol and branched-chain and/or straight-chain fatty acids of 6 to 18 carbon atoms. The partial coesterification of dicarboxylic acids is possible.

The fatty acid-polyol partial esters to be reacted always contain free hydroxyl groups of the polyols used, the amount of which is expressed by the hydroxyl number (measured in milligrams of potassium hydroxide per gram of ester).

The reacted silanes enter into a bond with these hydroxyl groups of the partial esters by the reaction of the epoxy group of the glycidyl moiety.

In the case of partial esters having contents of dicarboxylic acids, they, too, have the hydroxyl numbers in the above-mentioned range. The acid number is then preferably zero or very small. If, due to the way in which the reaction was conducted, the second carboxyl group of the dicarboxylic acids is not bound, a small or larger acid number, in addition to the hydroxyl number, can occur.

Neutral esters or full esters of the polyols with the said acids, however, have hydroxyl numbers and acid numbers of 0 or very small values. If esters are formed by the reaction of partial esters with a molar excess of dicarboxylic acids, the esters have a zero hydroxyl number and an acid number depending on the free carboxyl groups.

The preparation of such partial esters with defined hydroxyl group contents can be accomplished by known catalytic esterification of the polyol components with an amount of fatty acid lower than the stoichiometric, or by the reaction of full esters of the fatty acids or esters of the fatty acids and dicarboxylic acid in a transesterification with polyols, in accordance with European Pat. No. 0014 308, in the manner of a transesterification in the presence of alkali or acids.

The required organo-organo silanes are known and are available in the line of products of Dynamit Nobel A.G. Preferred are gamma-glycidoxypropyltrimethoxysilane, gammaglycidoxypropyltripropoxysilane or mixtures thereof. Fundamentally, silanes having an epoxy group in any kind of moiety as well as one to three alkoxy groups of any kind, as well as a supplemental number of inert moieties, can be used, but such silanes are difficult to obtain.

The viscose, gel-like ester mixtures are generally neutral esters with or without low hydroxyl and acid numbers.

For special purposes, it is possible, through the selection of the conditions of preparation and the amounts of the components, to obtain partial esters having hydroxyl numbers of 5 to 160 or carboxyl group-containing esters with acid numbers up to 150.

The ester mixtures of the invention are distinguished by the following special advantages:

1. They are odorless, homogeneous, viscous, gel-like ester mixtures of clear transparency which have a pleasant feel on the skin.
2. The stability of the viscous, gel-like ester mixtures is excellent, since the gel structure is formed by linkage through principal valences.
3. The viscous, gel-like ester mixtures obtained show no tendency to bleed oil when used in pharmaceutical and cosmetic preparations or as additives in technical formulations. Even solid-to-liquid phase changes are reversible.
4. They are largely soluble or dispersible in mineral oils of a paraffinic and aromatic nature, and can be used to adjust their viscosity.
5. Viscous, gel-like ester mixtures can be prepared with dropping points above 300° C.
6. The evaporation losses at elevated temperatures are minimized by the installation of the silane bond.
7. The viscous, gel-like ester mixtures have outstanding structurizing properties in creams and lotions.
8. The viscosity or gel quality of the ester mixtures can be as desired, depending on the installation of the organo-organo-oxysilanes in the fatty acid polyol partial ester.

Trialkoxysilane groups under reaction conditions of 100 to 240° C. can form, the siloxane group Si-O-SI under splitting off alcohol, but if desired the alkoxy groups can be partially preserved, or even entirely preserved in exceptional cases.

The viscous, gel-like ester mixtures can be prepared in the most general case by the reaction of the silane component with polyol esters, which preferably have hydroxyl groups corresponding to the hydroxyl numbers 5 to 150 and have monocarboxylic acid moieties as well as, if desired, dicarboxylic acid moieties, or with polyol esters which have carboxyl groups in corresponding amount with acid numbers from 5 to 150 due to contents of dicarboxylic acids. Also possible is the reaction of partial esters with less than the stoichiometric amount of the silane component.

The partial esters can be prepared prior to the reaction, by any desired method, and also esters with contents of carboxyl groups, using known esterification catalysts, especially titanic esters.

The reaction with the silanes takes place preferably in the presence of catalysts, such as Lewis acids of known kind, toluenesulfonic acid or aluminum chloride or stannous chloride.

The same catalysts are suitable in the siloxane-group condensation. Suitable catalysts are given in Ullmann, vol. 21, p. 515. If alkoxy groups are to be preserved, no alcohol or only a part of the alcohol is removed, or the temperature is kept low, at 120° to 140° C., for example.

Recommendable is a reduced pressure of 2 to 1000 mbar, especially 100 to 200 mbar.

Fatty acid polyol partial esters, which are difficult to prepare, as well as esters with contents of carboxyl groups, can be prepared directly before the reaction with the silane, from neutral esters, for example, or from the components, under transesterification or esterification conditions which are known in themselves, and their preparation can be performed in the same vessel. If a dicarboxylic acid component is to be contained, it can be obtained by adding the dicarboxylic acid or its derivatives, especially the anhydride mixtures, anhydrides or halides, particularly the chlorides.

Further subject matter of the invention is therefore a method for the preparation of viscous, gel-like ester mixtures wherein fatty acid-polyol partial esters or their mixtures, having hydroxyl numbers from 5 to 150, preferably 10 to 80, are reacted with 2 to 45 wt.-%, preferably 4 to 30 wt.-%, with respect to the ester or ester mixtures, of gamma-glycidoxypropyltrialkoxysilane having alkyl groups of 1 to 3 carbon atoms, at 20° to 210° C., preferably 60° to 120° C., and the trialkoxysilane groups of the silanes are condensed wholly or partially to siloxane-groups at 100° to 240° C., preferably 160° to 200° C., with the injection of steam at temperatures of 100° to 240° C., preferably 150° to 170° C., so as to form viscous, gel-like ester mixtures, or fatty acid-polyol partial esters having hydroxyl numbers from 5 to 150 are formed by reaction of fatty acid-polyol full esters by reaction with polyols, and then reacted with 2 to 45 wt.-% of gamma-glycidoxypropyltrialkoxysilanes and condensed siloxane-like in the same manner. Also, further subject matter of the invention is in a method whereby dicarboxylic acids or their anhydrides or halides are reacted, in amounts of 0.01 to 50 mole-% of hydroxyl groups of the polyols, are reacted with fatty acid-polyol partial esters to form esters having hydroxyl numbers from 5 to 150 prior to the reaction with gamma-glycidoxypropyltrialkoxysilanes, and the use of the viscous, gel-like ester mixtures as gelling agents or adjuvants in pharmaceutical or cosmetic preparations.

The invention furthermore relates to the use of the silane-modified ester mixtures as gelling agents or adjuvants in pharmaceutical or cosmetic preparations.

On account of the viscous, gel-like consistency of the ester mixtures, they can be especially suitable for use as gelling agents or as substances for increasing viscosity in oily preparations or in ointment preparations, or for the preparation of gels. Additions amounting to 2 to 80%, preferably 5 to 40%, and very preferably 5 to 15%, according to the viscosity of the ester mixtures, are sufficient.

The invention on the other hand relates to spreadable preparations with high strength of adhesion to the skin, on the basis of the viscous, gel-like, silane-modified ester mixtures, to serve as pharmaceutical or cosmetic preparations.

The preparation contains a component of oily consistency plus an active substance if desired, (or the component of oily consistency contains an active substance), as well as the new viscous, gel-like ester mixture, which brings about new, previously unknown properties in the preparation.

The term, "spreadable," as used in conjunction with the invention, refers to the ability to cover the human or animal skin as well as mucous membranes adjacent the surface, and the mucous membranes in the interior of the body, and to spread out thereon so as to form a uniform film. Accordingly, the invention relates to highly fluid preparations of all consistencies suitable for this purpose, ranging from highly fluid oils of low viscosity, up to creams, salves, emulsions and, especially, gels, which can be of a nature ranging from fluid oils up to stiff and punctureresistant gels.

There has long been a need for preparations which can be applied to the skin and which would have a better adherence thereto, be difficult to remove from the skin, and thus have a longer period of activity or permit longer protection of the skin.

Preparations of this kind, however, have not been available. Instead, the known preparations often have to be reapplied at least several times daily.

An important component of the new spreadable preparations is a new, viscous, gel-like ester mixture which consists of a product of the reaction of fatty acid-polyol partial esters having hydroxyl numbers from 5 to 150 with gamma-glycidoxypropyltrialkoxysilanes. If desired, one reactive component of the ester mixture can also be the radical of a dicarboxylic acid, especially an aliphatic dicarboxylic acid, in which case the dicarboxylic acid component then forms preferably a part of the partial ester of hydroxyl numbers 5 to 150.

The other components of the spreadable preparation need only to fulfill the condition of compatibility in pharmaceutical or cosmetic preparations and of being of an oily consistency.

Furthermore, pharmaceutical or cosmetic agents can be present in the oily preparations, in dissolved or dispersed form; they can be separately added, or they can be already a component of the ingredient of oily consistency.

In certain cases, however, the preparations have no pharmaceutical or cosmetic agents added to or contained in the oily ingredient, since the viscous, gel-like ester mixtures already possess certain novel pharmaceutical and cosmetic actions.

It has been found that the viscous, gel-like ester mixtures, which are described in detail below, have an extremely good adherence to the skin, to the mucous membranes and to human and animal body tissues of all kinds. This particularly good adherence is especially such that the preparations are difficult to remove from the skin. The skin area treated becomes difficult to wet, and in the case of numerous formulations it has a slight or even very high sheen. When washed with soap or detergents the preparations are not at first removable, yet the gel can be removed, depending on the content of the viscous gel-like ester mixture and its nature, by repeated washing with, for example, ordinary soap. Gels and other preparations can be made from the ester mixtures which are removable only by 5 to 6 washings or as many as 10 washings, so that removal by washing with soap in the conventional manner is utilized as a test of persistence on the skin.

On the other hand, the viscous, gel-like ester mixtures, and therefore the spreadable preparations made therefrom, can be completely absorbed by the skin after a relatively long period of time, without ill effect, while any active agents present, or the component of oily consistency, are absorbed by the skin more quickly, depending on their own penetrating characteristics.

The new viscous, gel-like ester mixtures furthermore have the remarkable property of being particularly stable gelling agents, so that portions of the viscous, gel-like ester mixtures can be used to adjust the viscosity of the component of oily consistency to any consistency up to that of a stiff gel. The tridimensional crosslinking by means of siloxane structure in the reaction product formed from silanes results in a tridimensional lattice structure, which, even with the addition of small amounts, permits gels to form which preserve the adjusted viscosity for very long periods of time, and which maintain that viscosity even at substantially elevated temperature, under tropical conditions, for example. In some cases the dropping temperatures of the viscous, gel-like ester mixtures are higher than 300° C. Furthermore, these viscous, gel-like ester mixtures are excellent emulsifiers, both for the preparation of water-in-oil emulsions and for the preparation of oil-in-water emulsions, and thus they make possible the preparation of salves, creams, lotions and the like. Also, the viscous, gel-like ester mixtures have a good spreading action on the skin, such that the natural oils in exposed skin or skin damaged by frequent washing are preserved, or a skin-care cream can have an oil-restorative action.

Special subject matter of the invention is a spreadable preparation having a high persistence on the skin, which consists of:

(a) 5 to 80 wt.-% of viscous, gel-like ester mixtures consisting of products of the reaction of fatty acid-polyol partial esters or their mixtures, with hydroxyl numbers of 5 to 150, preferably 10 to 80, with 2 to 45 wt.-%, with respect to the ester mixtures, of gamma-glycidoxypropyltrialkoxysilanes having alkyl groups of 1 to 3 carbon atoms, or mixtures thereof, or, in some cases, consisting of reaction products containing, as additional reaction components, dicarboxylic acids or their anhydrides or halides, in amounts of 0.01 to 50 mole-%, preferably 0.01 to 30 mole-%, per mole of hydroxyl groups in the polyols.

(b) 95 to 20 wt.-% of a component of oily consistency, or of a oil-in-water or water-in-oil emulsion of this component, and, in some cases:

(c) 0.01 to 20 wt.-% of an active agent or a liquid or solid preparation containing such agent.

As previously stated, only the spreadability of the preparation and a content of the viscous, gel-like ester mixtures are the necessary requirements for the preparation in accordance with the invention, while the contents of the viscous, gel-like ester mixture can also have percentages of less than 5 wt.-% or more than 80 wt.-%, and the rest of the components are optional, so long as a spreadable preparation for use in pharmaceutical and cosmetic preparations is the result.

Therefore, additional subject matter is the use of the preparations as pharmaceutical or cosmetic preparations, especially for the treatment of the skin.

The preparation can be used as a spray containing conventional diluents and propellants.

The preparations can be in the nature of oils, creams, salves, emulsions or gels of a consistency ranging from easily spreadable to puncture-resistant gels, it being possible especially to prepare clear gels of transparent to translucent character, depending on the clarity of the other components.

Unlike numerous gels or salves, the preparations have a pleasant feel on the skin, to which the viscous, gel-like ester mixtures contribute.

As already stated, the viscous, gel-like ester mixtures, as components of the preparations, bring about an extremely good adherence of the preparations to the skin and, when the percentage of the viscous, gel-like ester mixtures is high, they permit long intervals of time between treatments, but if the percentage of the viscous, gel-like ester mixtures is low, it can also be brought about that the treatment agent will be no longer detectable on the skin.

On account of the good gel-forming capacity of the ester mixtures, preparations in the form of gels, especially clear gels, along with any desired additional components and active agents, are special subject matter of the invention. Preparations which are not gel-like and not clear or transparent can satisfy the need for additional spreadable types of preparations and can also be prepared to advantage, especially in order to make use of the skin oil restoring properties and emulsifying qualities of the ester mixtures.

Additional subject matter of the invention is sunscreen and ultraviolet blocking preparations making use of the especially good adherence to the skin and persistence when the skin is washed with soap in the conventional manner. These sun-screens containing known light-blocking substances are suitable not only for protection against the sun in sports activities, such as hiking and skiing at high altitudes, and for summer vacationers, but also for industrial purposes, such as the protection of electric welders against ultraviolet radiation, or for the protection of the skin during therapeutic treatment with ultraviolet rays. The special advantage is that, due to the especially good persistence of the ester preparations, the parts of the skin treated with the sun-screen are not wettable in contact with water, for example during a day at the beach, and thus the common, very frequent use of sun-screen can be replaced by the easier application at longer intervals of time.

The preparations also have special value as skin protectants, for example in industry for protection against aggressive aqueous solutions, and also for skin protection in the household as a component of washing solutions containing tensides.

Gel preparations, especially clear gels, are preferred in many cases as sun-screens and skin protecting agents.

Examples of other preparations are massaging oils of any desired consistency, with contents of skin-treating agents such as eucalyptus oil or extracts of Hypericum perforatum or the like, oily preparations for treating the nasal mucosae, prepared especially from light liquid petrolatum, and containing, if desired, eucalyptus oil, ephedrine or other agents, lip ointments on a paraffin basis for use in protecting against strong solar radiation and chapping. Preparations for dentistry are also anticipated, with the advantage of good adhesion to the oral mucosae and teeth when the mouth is rinsed with water. Liquid or paste preparations with or without active substances are suitable for rectal application.

The additional component of oily consistency can be of any desired kind, as long as it is pharmacologically or cosmetically unobjectionable and desirable.

Suitable are fatty oils of natural and synthetic origin, the neutral oils synthetically prepared from glycerides, light liquid petrolatum, and, generally, esters of polyvalent alcohols of 2 to 4 carbon atoms, and saturated or unsaturated, straight-chain or branched monocarboxylic acids of 1 to 30 carbon atoms.

Preferred are so-called neutral oils which do not turn rancid, i.e., triglycerides of the saturated straight-chain fatty acids of 6 to 14, especially 8 to 12 carbon atoms, as well as corresponding triglycerides in which aliphatic dicarboxylic acids of 2 to 6 carbon atoms are contained in addition to the named saturated fatty acids.

It is to be understood that the component of oily consistency can be present in very small amounts or can even be omitted if the viscous, gel-like ester mixture contains only very small amounts of silanes as reaction components, in which case the active agent, if desired, is an oil pressed from vegetable matter and containing an active agent.

The manufacture of the preparations having contents of silane-modified ester mixtures can be performed by mixing the components, with intensive stirring or shearing action if necessary, with heating if desired.

In partial esters mentioned e.g. ethyleneglycol fatty acid diester will contain ethyleneglycol fatty acid monoester (HO—$CH_2$—$CH_2$—fatty acid) the amount of the latter will contribute OH-groups measured as hydroxyl number.

As gels or gel-like products of the invention is understood a behaviour of products being stiff and getting fluid or pasty when agitated by e.g. stirring and, when agitation is stopped, loosing this flowable and pourable state some time later to stiffen again to a not pourable state; this behaviour e.g. being able to stiffen oils by addition of the products of the invention, will contribute the valuable characteristics to the claimed preparations.

EXAMPLES

EXAMPLE 1 (Viscous, gel-like ester mixture)

In a one-liter flask with ground glass stopper, provided with stirrer, water separator, thermometer and gas introduction tube, a mixture of 150 g of triethylene glycol, 426 g of isostearic acid and 0.1 g of tetrabutyl titanate is heated, with stirring, to 240° C. at 760 mbar, and then, at the same temperature, the pressure is lowered to 100 mbar over a period of 6 hours. The partial ester thus formed has an acid number of less than 1 and a hydroxyl number of 52. After cooling to 100° C., 105 g of gamma-glycidoxypropyltrimethoxysilane is added, plus 1 g of aluminum chloride as catalyst, and the mixture is stirred. At 180° C. and 100 mbar, the passage of steam through the reaction mixture is begun at a steam temperature of 130° C. The steaming is continued until no more methanol is formed. At the same time, methanol and water are continously removed as vapors. Parallel thereto, the viscosity of the silane-modified ester mixture increases and a clear, transparent oleogel is formed.

Acid number: less than 2.
Viscosity at 20° C. =47,500 mPa.s
Hydroxyl number: 40.

EXAMPLE 2 (Viscous, gel-like ester mixture)

At the reaction temperature described in Example 1, a mixture of 80 g of 1,2-propanediol, 450 g of oleic acid and 0.1 g of tetrabutyltitanate is esterified under the described reaction conditions to a partial ester with an acid number of 0.6 and a hydroxyl number of 55. At 80° C. and 1000 mbar, 136 g of gamma-glycidoxypropyltriethoxysilane is added on, in the presence of 0.5 g of stannous chloride. Then, at 140° C. and 40 mbar, steam at 120° C. is introduced into the reaction mixture. The steam injection continues until the formation of ethanol ends. A viscous, gel-like ester mixture is obtained, which has a spreadable and transparent consistency.

Viscosity at 20° C.=37,600 mPa.s
Hydroxyl number: 39

EXAMPLE 3 (Viscous, gel-like ester mixture)

In a one-liter flask with ground-glass stopper, equipped with stirrer, water separator, thermometer and gas introduction tube, 500 g of a triglyceride mixture of adipic acid and saturated vegetable fatty acid of an average chain length of 8 to 10 carbon atoms, plus 6 g of glycerol and 0.1 g of tetrabutyltitanate, were heated for 4 hours at 240° C., with stirring, while simultaneously passing inert gas through the reactor, 0.55 mole of adipic acid and 1.9 mole of the vegetable fatty acid being esterified per mole of glycerol. The hydroxyl number of the reaction mixture achieved by transesterification amounts to 26. To this reaction mixture, in the form of succinic acid condensed fatty acid partial glyceride, 52 g of gamma-glycidoxypropyltrimethoxysilane and 1 g of aluminum chloride are added, and the mixture is stirred for one-half hour at 100° C. and 1000 mbar. Then, at 180° C. and 80 mbar, steam at a temperature of 160° C. is passed through the silane-modified fatty acid partial ester. The methanol that forms and the steam are removed as vapors. The viscosity of the silane-modified fatty acid partial ester increases as the methanol forms, and when the production of methanol ends, a clear, transparent gel results.

Acid number: 0.7
Saponification number: 394
Hydroxyl number: 22
Viscosity at 20° C.: 10800 mPa.s
Dropping point: above 300° C.

EXAMPLE 4 (Viscous, gel-like ester mixture)

In the manner described in Example 3, 500 g of a triglyceride prepared from saturated coconut oil fatty acids of 8 to 18 carbon atoms and a hydroxyl number of 9, and 12 g of glycerol, are transesterified in the presence of 0.1 g of tetrabutyltitanate to form a fatty acid partial glyceride of hydroxyl number 49. The next reaction with 139 g of gammaglycidoxypropyltripropoxysilane and 2 g of stannous chloride is performed at 120° C. and 1000 mbar. Then, at 200° C. and 50 mbar, the injection of steam is performed, at steam temperatures of 170° C., over a period of 6 hours, to form a highly viscous oleogel.

Acid number: 0.8 mPa.s
Hydroxyl number: 35
Viscosity at 52° C.: 83000
Melting point: 39.5° C.

EXAMPLE 5a (Viscous, gel-like ester mixture)

In the manner described in Example 1, a mixture of 114 g of trimethylolpropane and 555 g of isostearic acid is esterified in the presence of 0.2 g of tetrabutyltitanate to form a partial ester with a hydroxyl number of 59. The adding on of 156 g of gamma-glycidoxypropyltrimethoxysilane is performed in the presence of 2 g of aluminum chloride at 100° C. and 1000 mbar. The silane-modified partial ester is filtered to remove the catalyst and then gelled by the injection of steam at steam temperatures of 160° to 180° C. and 80 mbar. During four hours of reaction time methanol and water are removed as vapors.

Acid number: 1.4
Hydroxyl number: 48
Viscosity at 20° C.: 82000 mPa.s

EXAMPLE 5b (Use and formulation)

The solubility and viscosity of the silane-modified trimethylolpropane-isostearate gel prepared in Example 5a is tested in a mixture with trimethylolpropanetriisostearate. The various proportions of viscous, gel-like ester mixture and ester components are weighed into the beaker and stirred at 20° to 25° C. Viscous to gel-like clear solutions and gel systems are formed.

| Weight-percent of oleogel | Weight-percent of ester | Viscosity at 30° C. [mPa.s] |
|---|---|---|
| 0 | 100 | 135 |
| 20 | 80 | 840 |
| 40 | 60 | 4380 |
| 50 | 50 | 10500 |
| 60 | 40 | 18000 |
| 80 | 20 | 47500 |
| 100 | 0 | 82000 |

Oleogels with a similar gradation of viscosity are obtained by mixing the substances of Examples 1 to 5a with fatty oils, preferably transesterification oils which do not turn rancid and are prepared from glycerol and saturated straight-chain monocarboxylic acids of a chain length of 8 to 12 carbon atoms, and with oils pressed from plants or extracted oils, which contain active substances.

EXAMPLE 6 (Viscous, gel-like ester mixture)

In the manner described in Example 1, 82 g of pentaerythritol and 613 g of isostearic acid are esterified in the presence of 0.1 g of tetrabutyl titanate to form a pentaerythritol partial ester having a hydroxyl number of 20. The adding on of 55 g of gamma-glycidoxypropyltrimethoxysilane is performed at 100° C. in the presence of 1 g of aluminum chloride. When steam is injected at steam temperatures from 160° to 180° C. and 80 mbar, the reaction mixture condenses within 6 hours to a clear, viscous, gel-like ester mixture with the release of methanol.

Hydroxyl number: 14
Viscosity at 30° C.: 4800 mPa.s.

EXAMPLE 7 (Viscous, gel-like ester mixture)

In the manner of Example 1, 82 g of pentaerythritol and 562 g of isostearic acid are esterified in the presence of 0.1 g of tetrabutyl titanate to form a pentaerythritol partial ester having a hydroxyl number of 40. The adding on of 102 g of gamma-glycidoxypropyltrimethoxysilane is performed in the presence of 1 g of aluminum chloride at 100° C. When steam is injected at steam temperatures of 160° to 180° C. and 80 mbar, the reaction mixture condenses in 7 hours to a clear, viscous oleogel with the release of methanol. Hydroxyl number: 32 Viscosity at 30° C.: 36000 mPa.s.

EXAMPLE 8 (Viscous, gel-like ester mixture)

As described in Example 1, 82 g of pentaerythritol and 511 g of isostearic acid are esterified in the presence of 0.1 g of tetrabutyl titanate to a pentaerythritol partial ester having a hydroxyl number of 60. The adding on of 141 g of gamma-glycidoxypropyltrimethoxysilane is performed at 100° C. in the presence of 1 g of aluminum chloride. When steam is injected at steam temperatures of 160° to 170° C. and 80 mbar, the reaction mixture condenses in 8 hours to a clear, highly viscous oleogel with the release of methanol.

Hydroxyl number: 55
Viscosity at 30° C.: 98000 Pa.s.

EXAMPLE 9 (Formulation)

The sunscreen gel 1a and the viscous sunscreen oil 1b are prepared by combining the components in a stirring vessel and stirring them at 40° C. until uniformly distributed.

| Example | 1a | 1b |
|---|---|---|
| Viscous ester mixture of Example 4 | 50 wt. parts | 10 wt. parts |
| Neutral ester I** | 50 wt. parts | 90 wt. parts |
| Neo-Heliopan* | 5 wt. parts | 5 wt. parts |

*Light filtering substance made by Haarmann and Reimer of Holzminden
**Mixed-acid triglyceride from 2.1 mol of saturated fatty acids of eight to ten carbon atoms chain length and 0.45 mol of succinic acid.

Both products produce a pleasant feel on the skin. Product 1b produces a visible sheen, product 1a a strong sheen. The skin becomes unwettable.

Product 1a is subjected to a washing test by conventionally washing the skin with soap: After the 3rd washing, water still rolls in beads from the skin; not until after the 5th washing has the product been largely removed, and after the 8th washing it is almost entirely removed.

For comparison, a gel prepared from the neutral ester I and an organically modified montmorillonite (Bentone®, NL-Industries, Inc., Highstown, N.J., USA) is stirred in sufficient quantity to produce the same viscosity. This gel is removed by the first washing with soap.

EXAMPLE 10 (Formulation)

By mixing 20 parts of the product of Example 5 with 80 parts of neutral oil II (triglyceride of saturated fatty acids of a mean chain length of 8 to 10 carbon atoms) and 10 parts of eucalyptus oil, a viscous oil is prepared as nose drops for the treatment of colds. Other active substances such as ephedrine, for example in amounts of 0,5 to 1,0 wt.-% of the product, can be added. The product distributes itself in small amounts uniformly on the nasal mucosae. Not until several hours later is another application needed.

EXAMPLE 11 (Formulation)

By mixing together 20 parts of the product of Example 5 with 80 parts of neutral oil II and 5 parts of a mixture of equal proportions of balm mint oil, mugho pine oil and St. John's-wort oil (*Oleum hyperici*), a rubbing oil is prepared which can be spread easily and uniformly and, even after brief rubbing, transfers no oily components to the clothing.

It will be understood that the specification and examples are illustrative but not limitative of the present invention and that other embodiments within the spirit and scope of the invention will suggest themselves to those skilled in the art.

We claim:

1. An ester mixture comprising a reaction product of a fatty acid polyol partial ester, or a mixture of such esters, with hydroxyl numbers of 5 to 150, preferably 10 to 80, and 2 to 45 wt.-%, preferably 4 to 30 wt.-%, with respect to the ester or their mixtures, of gamma-glycidoxypropyltrialkoxysilane with alkyl groups of 1 to 3 carbon atoms or their mixtures.

2. The ester mixture of claim 1, further comprising as an additional reacted component, dicarboxylic acids or their anhydrides or halides in amounts from 0.01 to 50 mole-%, preferably 0.01 to 30 mole-percent, per mole of OH groups of the polyol partial ester.

3. A method of preparing an ester mixture comprising: reacting a fatty acid polyol partial ester or a mixture of such esters, having hydroxyl numbers from 5 to 150, preferably 10 to 80, with 2 to 45 wt.-%, preferably 4 to 30 wt.-%, with respect to the ester or their mixtures, of gamma-glycidoxypropyltrialkoxysilane with alkyl groups of 1 to 3 carbon atoms, at 20° to 210° C., and preferable 60° to 120° C.

4. The method of claim 3, wherein trialkoxysilane groups of the silanes are condensed to siloxane Si—O—Si groups wholly or partially at 100° to 240° C., preferably at 160° to 200° C.

5. The method of claim 3, the fatty acid polyol partial esters having hydroxyl numbers from 5 to 150 are reaction products of fatty acid polyol full esters and polyols.

6. The method of claim 3, wherein dicarboxylic acids or their anhydrides or halides are reacted in amounts of 0,01 to 50 mole-% OH groups of the polyols with fatty acid polyol partial esters to form those of hydroxyl numbers from 5 to 150 prior to the reaction with gamma-glycidoxypropyltrialkoxysilane.

7. Use of the substances of claim 1 as gel formers or adjuvants in pharmaceutical or cosmetic preparations.

8. Use of the substances of claim 2 as gel formers or adjuvants in pharmaceutical or cosmetic preparations.

9. A spreadable topical preparation comprising
   (a) 5 to 80 wt.-% of a gel-like ester mixture comprising a reaction product of a fatty acid polyol partial ester or a mixture of such esters with hydroxyl numbers from 5 to 150, preferably 10 to 80, with 2 to 45 wt.-%, preferably 4 to 30 wt.-% with respect to the ester or ester mixture, of gamma-glycidoxypropyltrialkoxysilanes with alkyl groups of 1 to 3 carbon atoms, or their mixtures,
   (b) 95 to 20 wt.-% of a component of oily consistency or of a W/O or O/W emulsion of this component and water, and, if desired,
   (c) 0.01 to 20 wt.-% of an active agent or its liquid or, in some cases, solid preparation.

10. The preparation of claim 9, wherein the ester mixture further comprises reaction products which contain as additional reaction components dicarboxylic acids or their anhydrides or halides in amounts of 0.01 to 50 mole-%, preferably 0.01 to 30 mole-%, per mole of hydroxyl groups of the polyols.

11. Use of the preparation of claim 9 as a pharmaceutical or cosmetic preparation for the treatment of the skin.

12. Use, in accordance with claim 10, as a skin protector or sunscreen or radiation screen.

13. A pharmaceutical or cosmetic preparation for the treatment of skin comprising an effective amount of the preparation of claim 9.

14. A pharmaceutical or cosmetic preparation for the treatment of skin comprising an effective amount of the preparation of claim 10.

15. A skin proetector comprising an effective amount of the preparation of claim 9.

16. A skin protector comprising an effective amount of the preparation of claim 10.

* * * * *